United States Patent
Ikeda et al.

(10) Patent No.: US 10,521,912 B2
(45) Date of Patent: Dec. 31, 2019

(54) IMAGE PROCESSING APPARATUS

(71) Applicants: Canon Medical Systems Corporation, Otawara-shi (JP); FUJITA ACADEMY, Toyoake-shi (JP)

(72) Inventors: Yoshihiro Ikeda, Sakura (JP); Takashi Ichihara, Nagoya (JP); Takahiro Natsume, Toyoake (JP)

(73) Assignees: Canon Medical Systems Corporation, Otawara-shi (JP); FUJITA ACADEMY, Toyoake-shi (JP)

( * ) Notice: Subject to any disclaimer, the term of this patent is extended or adjusted under 35 U.S.C. 154(b) by 111 days.

(21) Appl. No.: 15/917,180

(22) Filed: Mar. 9, 2018

(65) Prior Publication Data
US 2018/0330502 A1  Nov. 15, 2018

(30) Foreign Application Priority Data
Mar. 9, 2017 (JP) ................................ 2017-045183

(51) Int. Cl.
*A61B 6/03* (2006.01)
*G06T 7/00* (2017.01)
*A61B 6/00* (2006.01)

(52) U.S. Cl.
CPC ............ *G06T 7/0016* (2013.01); *A61B 6/032* (2013.01); *A61B 6/481* (2013.01); *A61B 6/503* (2013.01); *A61B 6/541* (2013.01); *G06T 7/0012* (2013.01); *G06T 2207/10016* (2013.01); *G06T 2207/10081* (2013.01); *G06T 2207/20072* (2013.01); *G06T 2207/20104* (2013.01); *G06T 2207/20224* (2013.01); *G06T 2207/30048* (2013.01); *G06T 2207/30104* (2013.01)

(58) Field of Classification Search
CPC .................................... G06T 7/00; A61B 6/00
USPC .......................................................... 382/131
See application file for complete search history.

(56) References Cited

U.S. PATENT DOCUMENTS

2010/0272344 A1* 10/2010 Ichihara ................. A61B 6/032
                                                           382/132
2013/0225958 A1*  8/2013 Ichihara ................. A61B 6/481
                                                           600/363

FOREIGN PATENT DOCUMENTS

JP   2010-246725   11/2010
JP   2010-274106   12/2010
JP    2012-90883    5/2012

* cited by examiner

*Primary Examiner* — Abolfazl Tabatabai
(74) *Attorney, Agent, or Firm* — Oblon, McClelland, Maier & Neustadt, L.L.P.

(57) ABSTRACT

An image processing apparatus according to an embodiment includes processing circuitry. The processing circuitry is configured to acquire pieces of change information indicating temporal changes in computed tomography (CT) values of a myocardium and a right ventricular of a subject based on a plurality of chronologically consecutive images that are generated by an X-ray CT apparatus by scanning the subject to which a contrast agent is administered. The processing circuitry is configured to correct the piece of change information on the myocardium based on the piece of change information on the right ventricular.

10 Claims, 11 Drawing Sheets

IMAGE PROCESSING APPARATUS

CROSS-REFERENCE TO RELATED APPLICATIONS

This application is based upon and claims the benefit of priority from Japanese Patent Application No. 2017-045183, filed on Mar. 9, 2017; the entire contents of which are incorporated herein by reference.

FIELD

Embodiments described herein relate generally to an image processing apparatus.

BACKGROUND

As an examination for analyzing a myocardial blood flow, myocardial perfusion is known. For example, in the myocardial perfusion, an X-ray computed tomography (CT) apparatus obtains a time-density curve (TDC) indicating a temporal change in a CT value of an aorta and a TDC indicating a temporal change in a CT value of a myocardium from X-ray CT images that are generated by capturing chronological images of a subject to which a contrast agent is administered. Then, by solving a transfer function or a compartment model using the TDC of the aorta as input and the TDC of the myocardium as output, a myocardial blood flow rate is calculated.

DETAILED DESCRIPTION

An image processing apparatus according to an embodiment includes processing circuitry. The processing circuitry is configured to acquire pieces of change information indicating temporal changes in computed tomography (CT) values of a myocardium and a right ventricular of a subject based on a plurality of chronologically consecutive images that are generated by an X-ray CT apparatus by scanning the subject to which a contrast agent is administered. The processing circuitry is configured to correct the piece of change information on the myocardium based on the piece of change information on the right ventricular.

Exemplary embodiments of an image processing apparatus will be described below with reference to the drawings. A medical information processing system including the image processing apparatus will be described below as an example. Possible embodiments are not limited to the embodiments described below. Contents described in one embodiment are similarly applicable to any other embodiment in principle.

First Embodiment

Figure 1:
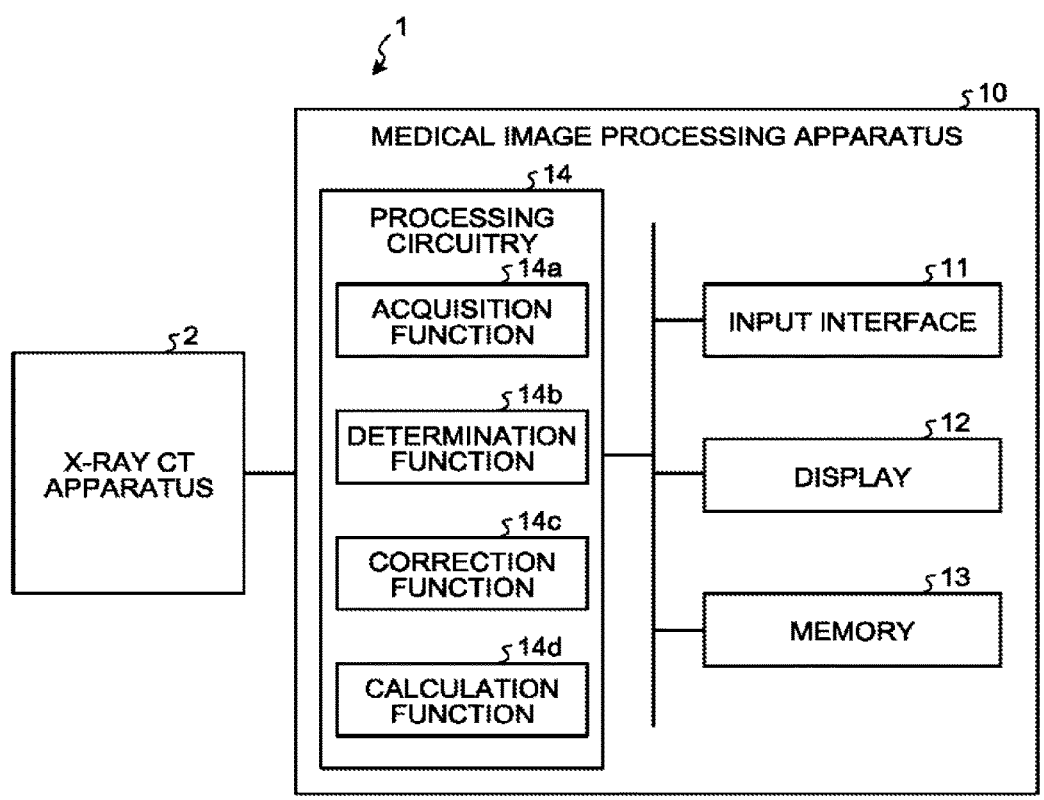
FIG. 1 is a block diagram illustrating a configuration example of a medical information processing system according to a first embodiment.

FIG. 1 is a block diagram illustrating a configuration example of a medical information processing system 1 according to a first embodiment. As illustrated in FIG. 1, the medical information processing system 1 according to the first embodiment includes an X-ray CT apparatus 2 and a medical image processing apparatus 10. The X-ray CT apparatus 1 and the medical image processing apparatus 10 are enabled to directly or indirectly communicate with each other over an in-hospital local area network (LAN) installed in a hospital, for example. For example, when a picture archiving and communication system (PACS) is introduced in the medical information processing system 1, the apparatuses mutually transmit and receive medical images or the like in accordance with a digital imaging and communication in medicine (DICOM) standard. Here, supplementary information includes, for example, a subject identifier (ID) for identifying a subject, an examination ID for identifying an examination, an apparatus ID for identifying each of the apparatuses, a series ID for identifying a single shot of imaging performed by each of the apparatuses, and the like.

Figure 2:
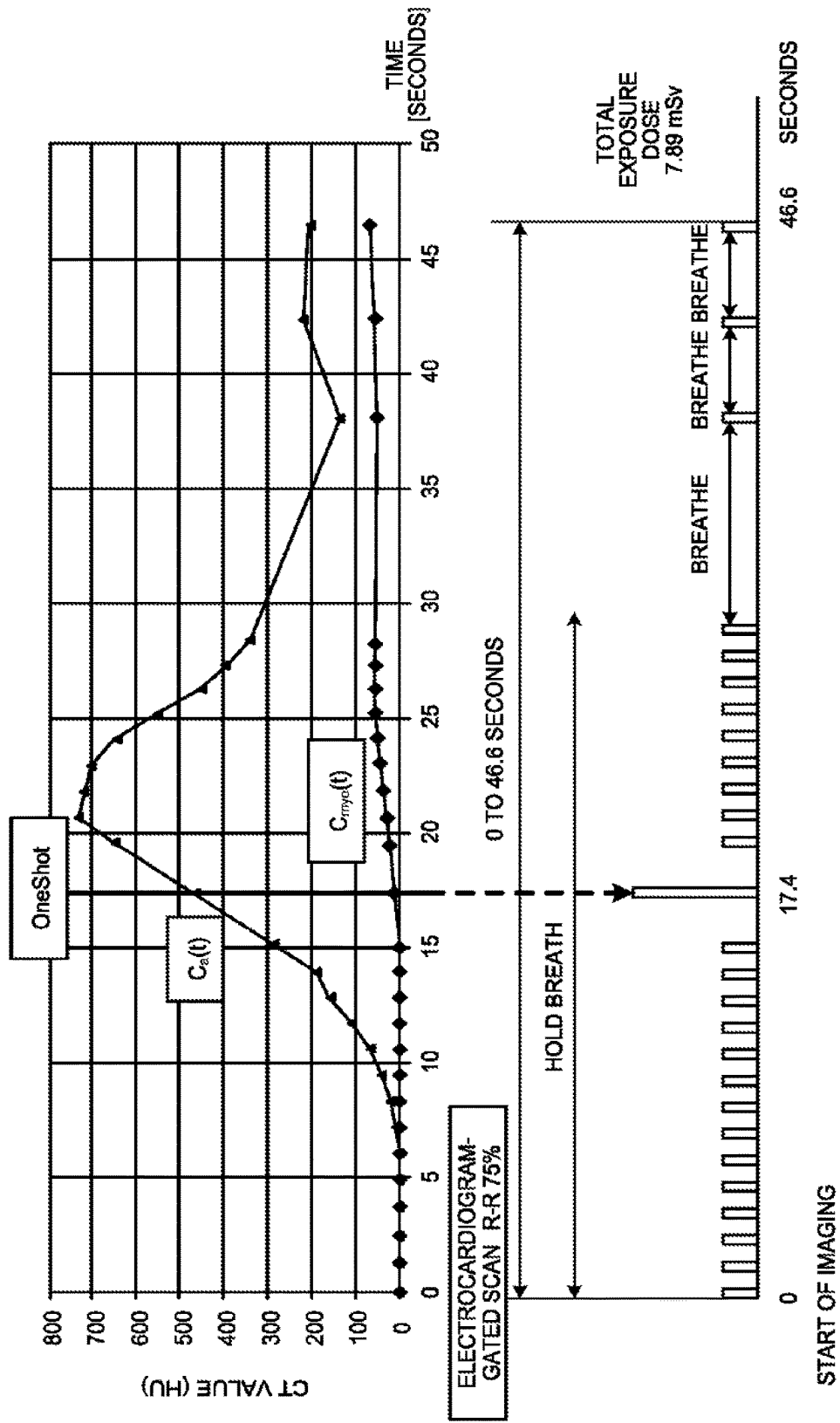
FIG. 2 is a diagram illustrating an example of an imaging protocol used by an X-ray CT apparatus according to the first embodiment.

The X-ray CT apparatus 2 reconstructs X-ray CT images based on projection data collected by scanning a subject. The X-ray CT apparatus 2 is connected to an electrocardiograph (not illustrated), and detects a cardiac cycle of a heart of the subject based on an electrocardiographic signal output from the electrocardiograph. For example, when imaging the heart, the X-ray CT apparatus 2 performs electrocardiogram-gated scan, in which imaging is performed in synchronization with the cardiac cycle of the heart using a contrast agent. More specifically, the X-ray CT apparatus 2 performs the electrocardiogram-gated scan on the whole heart of a subject to which a contrast agent is administered in the myocardial perfusion, and generates a plurality of chronologically consecutive X-ray CT images. FIG. 2 is a diagram illustrating an example of an imaging protocol used by the X-ray CT apparatus 2 according to the first embodiment.

A lower diagram in FIG. 2 indicates a timing of X-ray exposure in the electrocardiogram-gated scan performed by the X-ray CT apparatus 2. For example, the X-ray CT apparatus 2 sets a time from the first X-ray exposure to the last X-ray exposure to 44.6 seconds. In this case, when the X-ray CT apparatus 2 defines a cardiac phase by assuming that a range from a certain R-wave to a next R-wave corresponds to 0% to 100%, the X-ray CT apparatus 2 performs X-ray exposure at a timing corresponding to 75%. For example, the X-ray CT apparatus 2 performs X-ray exposure at the timing corresponding to 75% of the cardiac phase while a subject holds breath for about 30 seconds from the start of imaging, subsequently provides a breathing period, and then repeats the X-ray exposure at the timing corresponding to 75% of the cardiac phase and the breathing period. In addition, after a lapse of 17.4 seconds from the start of imaging, the X-ray CT apparatus 2 performs "one shot" scan using a higher X-ray exposure dose than those used at other timings. A total exposure dose to the subject due to the electrocardiogram-gated scan illustrated in the lower diagram in FIG. 2 is 7.89 millisieverts (mSv).

An upper diagram in FIG. 2 illustrates time-density curves (TDCs) indicating temporal changes in CT values. The TDCs illustrated in the upper diagram in FIG. 2 are generated from X-ray CT images that are reconstructed based on projection data collected by the imaging protocol illustrated in the lower diagram in FIG. 2. In the upper diagram in FIG. 2, for example, a TDC ($C_a(t)$) of a coronary artery and a TDC ($C_{myc}(t)$) of a myocardium are illustrated. Each of the TDCs illustrated in the upper diagram in FIG. 2 is a TDC for which a baseline is corrected. As illustrated in the upper diagram in FIG. 2, at the timing of "one shot", the CT value of the coronary artery increases. That is, at the timing of "one shot", the coronary artery is colored with the contrast agent, and by performing scan with a higher radiation dose at this timing than those used at other timings, it is possible to clearly draw the coronary artery. The TDCs may be generated by the X-ray CT apparatus 2 or may be generated by the medical image processing apparatus 10 as will be described later.

The X-ray CT apparatus 2 transmits the generated X-ray CT images to the medical image processing apparatus 10. When a medical image storage apparatus or the like is provided in the medical information processing system 1 for example, the X-ray CT apparatus 2 may transmit the generated X-ray CT image to the medical image storage apparatus.

The description returns to FIG. 1. As illustrated in FIG. 1, the medical image processing apparatus 10 according to the first embodiment includes an input interface 11, a display 12, a memory 13, and processing circuitry 14, and processes the X-ray CT images generated by the X-ray CT apparatus 2, or the like.

The input interface 11 corresponds to, for example, a mouse, a keyboard, a button, a touch panel, or the like. The input interface 11 receives various setting requests from an operator, and appropriately transfers the received various setting requests to the processing circuitry 14.

The display 12 displays a graphical user interface (GUI) used by the operator to input various setting requests with the input interface 11, and displays a processing result obtained by the processing circuitry 14, or the like.

The memory 13 is, for example, a semiconductor memory device, such as a random access memory (RAM) or a flash memory, or a storage device, such as a hard disk or an optical disk. The memory 13 stores therein a control program, various kinds of data, or the like for causing the medical image processing apparatus 10 to perform various processes.

The processing circuitry 14 controls operation of the medical image processing apparatus 10. As illustrated in FIG. 1, the processing circuitry 14 executes an acquisition function 14a, a determination function 14b, a correction function 14c, and a calculation function 14d. For example, various processing functions implemented by the acquisition function 14a, the determination function 14b, the correction function 14c, and the calculation function 14d as components of the processing circuitry 14 illustrated in FIG. 1 are recorded in the memory 13 in the form of a computer-executable program. The processing circuitry 14 is a processor that reads each of the programs from the memory 13 and executes the programs to implement functions corresponding to each of the programs. In other words, after reading each of the programs, the processing circuitry 14 has each of the functions illustrated in the processing circuitry 14 in FIG. 1.

The configurations of the apparatuses included in the medical information processing system 1 have been described above. In the medical information processing system 1 configured as above, the medical image processing apparatus 10 calculates a myocardial blood flow rate in myocardial perfusion. For example, the medical image processing apparatus 10 generates, from X-ray CT images generated by the X-ray CT apparatus 2, change information indicating a temporal change in a CT value of an aorta and change information indicating a temporal change in a CT value of a myocardium. In the following, a case will be described in which the medical image processing apparatus 10 generates, as the change information, a time-density curve (TDC) indicating a temporal change in the CT value, for convenience of explanation. The medical image processing apparatus 10 calculates a myocardial blood flow rate by solving a transfer function using the TDC of the aorta as input and the TDC of the myocardium as output, for example.

Figure 3:
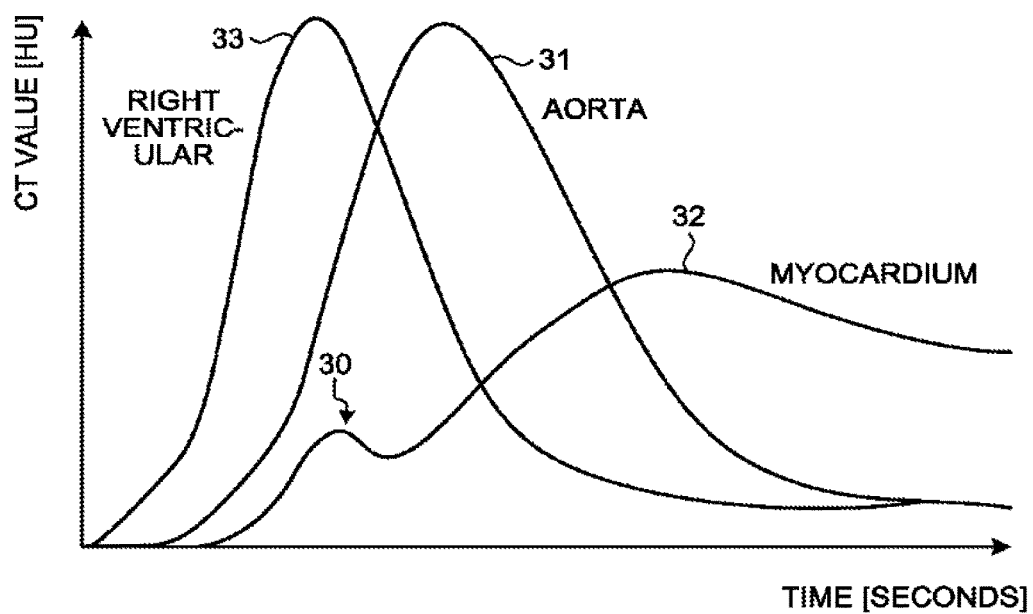
FIG. 3 is a diagram for explaining a conventional technology.

Incidentally, the TDC of the myocardium generated from the X-ray CT images may be influenced by an artifact from a right ventricular in some cases. For example, when the right ventricular and the left ventricular are deeply colored by administration of a contrast agent, and if only a signal of the myocardium is low, a signal of the myocardium between high signals of the right ventricular and the left ventricular increases. In this case, for example, the TDC of the myocardium has a local peak at the same timing as the TDC of the right ventricular. FIG. 3 is a diagram for explaining a conventional technology.

In FIG. 3, a TDC 31 of the aorta, a TDC 32 of the myocardium, and a TDC 33 of the right ventricular are illustrated. The vertical axis in FIG. 3 represents a CT value (HU), and the horizontal axis in FIG. 3 represents a time (seconds). For example, as illustrated in FIG. 3, the TDC 32 of the myocardium has a local peak 30 at around a peak of the TDC 33 of the right ventricular. In this case, the medical image processing apparatus 10 solves a transfer function using the TDC 32 of the myocardium including the artifact as output; therefore, it becomes difficult to accurately calculate a myocardial blood flow rate. Therefore, in the myocardial perfusion, it is important to accurately recognize a shape of the TDC of the myocardium without an influence of the artifact. At the local peak 30 of the TDC 32 of the myocardium, the CT value of the TDC 32 of the myocardium has a maximum value.

In view of the foregoing situations, the medical image processing apparatus 10 according to the first embodiment corrects the TDC of the myocardium based on the TDC of the right ventricular. For example, the medical image processing apparatus 10 corrects the TDC of the myocardium in a predetermined period based on a time at which the CT value of the TDC of the right ventricular indicates a peak. This process is realized by the processing circuitry 14 of the medical image processing apparatus 10. The process performed by the processing circuitry 14 of the medical image processing apparatus 10 will be described in detail below.

Figure 4:
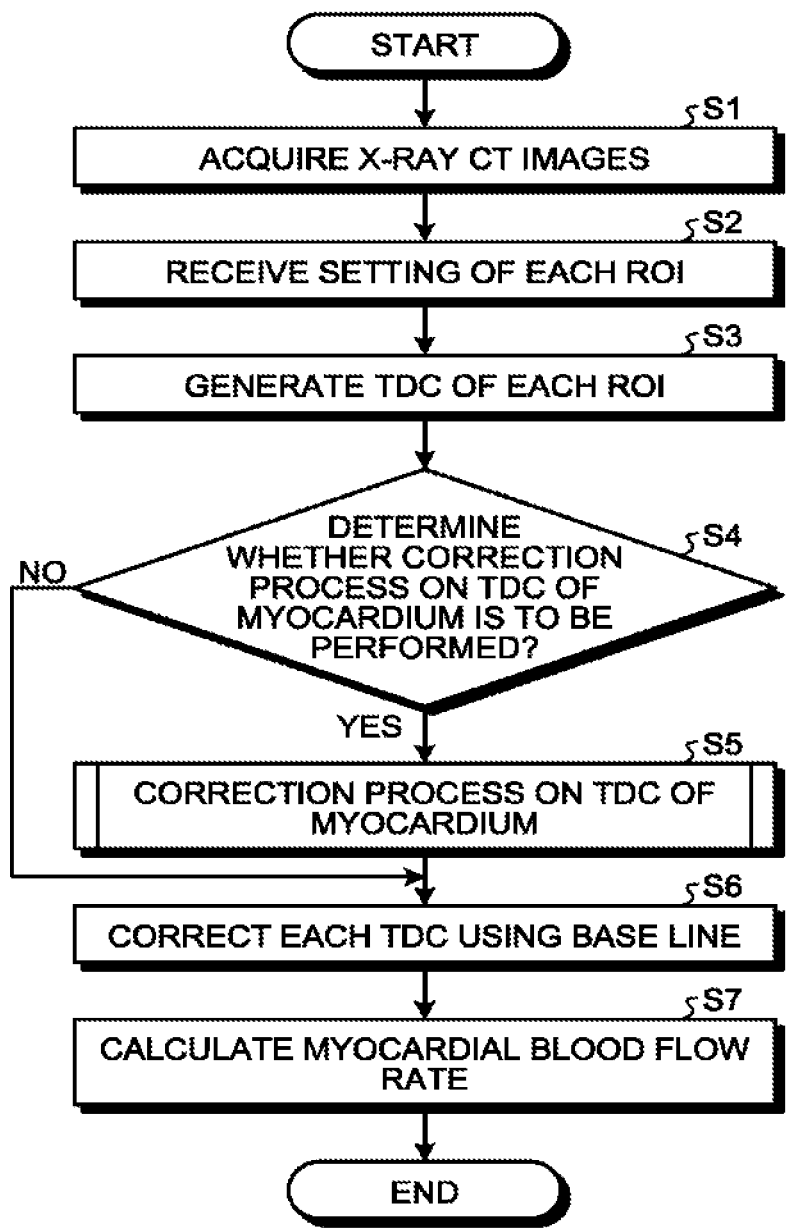
FIG. 4 is a flowchart illustrating a procedure in a process performed by processing circuitry according to the first embodiment.

FIG. 4 is a flowchart illustrating a procedure in the process performed by the processing circuitry 14 according to the first embodiment. In FIG. 4, a flowchart for explaining entire operation of the processing circuitry 14 is illustrated, and correspondence between the components and steps of the flowchart will be described below.

Step S1 to Step S3 are steps corresponding to the acquisition function 14a. At these steps, the processing circuitry 14 calls a predetermined program corresponding to the acquisition function 14a from the memory 13 and executes the program, so that the acquisition function 14a is implemented.

At step S1, the acquisition function 14a acquires X-ray CT images of a heart, for example. For example, the acquisition function 14a acquires, from the X-ray CT apparatus 2, a plurality of chronologically consecutive images that are generated by the X-ray CT apparatus 2 by scanning a subject to which a contrast agent is administered. When X-ray CT images generated by the X-ray CT apparatus 2 are stored in the medical image storage apparatus, the acquisition function 14a may acquire X-ray CT images of the heart from the medical image storage apparatus.

Figure 5:
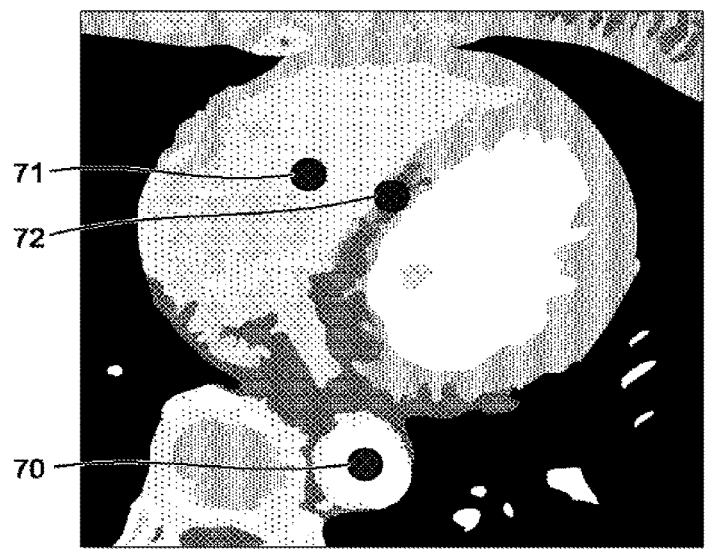
FIG. 5 is a diagram for explaining the first embodiment.

At step S2, the acquisition function 14a receives setting of a region of interest (ROI). For example, the acquisition function 14a receives setting of an ROI in each of a right ventricular, a myocardium, and a supply site that supplies blood to the myocardium. The supply site that supplies blood to the myocardium is, for example, any of an aorta, a left ventricular, and a coronary artery. In other words, the supply site that supplies blood to the myocardium is a blood vessel, and is, for example, the aorta, a blood vessel of the left ventricular, and the coronary artery. In the following, a case will be described in which the supply site that supplies blood to the myocardium is the aorta. FIG. 5 is a diagram for explaining the first embodiment.

An X-ray CT image illustrated in FIG. 5 is one example of the X-ray CT images acquired at Step S1. The acquisition function 14a receives setting of an ROI 71 in the right ventricular, an ROI 72 in the myocardium, and an ROI 70 in the aorta from a user via the input interface 11. FIG. 5 illustrates a case in which the acquisition function 14a receives setting of a single ROI in each of the right ventricular, the myocardium, and the aorta; however, possible embodiments are not limited to this example. For example, the acquisition function 14a may receive setting of a plurality of ROIs in any of the right ventricular, the myocardium, and the aorta. Further, the acquisition function 14a may receive setting of an ROI in a pixel unit, or may receive setting of an ROI including a plurality of pixels.

The description returns to FIG. 4. At Step S3, the acquisition function 14a generates a TDC of each of the ROIs. For example, the acquisition function 14a generates a TDC of the right ventricular indicating a temporal change in a CT value of the ROI 71 of the right ventricular, and a TDC of the myocardium indicating a temporal change in a CT value of the ROI 72 of the myocardium. That is, the acquisition function 14a acquires TDCs indicating temporal changes in the CT values of the myocardium and the right ventricular of a subject based on a plurality of chronologically consecutive images that are generated by the X-ray CT apparatus 2 by scanning the subject to which a contrast agent is administered. Further, for example, the acquisition function 14a generates a TDC of the aorta indicating a temporal change in a CT value of the ROI 70 of the aorta. That is, the acquisition function 14a acquires the TDC of the supply site that supplies blood to the myocardium based on a plurality of chronologically consecutive images that are generated by the X-ray CT apparatus 2 by scanning the subject to which a contrast agent is administered.

Step S4 is a step corresponding to the determination function 14b. At this step, the processing circuitry 14 calls a predetermined program corresponding to the determination function 14b from the memory 13 and executes the program, so that the determination function 14b is implemented. At Step S4, the determination function 14b determines whether a correction process on the TDC of the myocardium is to be performed.

For example, the TDC of the myocardium generated from the X-ray CT images may be influenced by an artifact from the right ventricular in some cases. If there is an influence of the artifact from the right ventricular, it is desirable to perform a correction process on the TDC of the myocardium. Therefore, the determination function 14b determines whether a process of correcting the TDC of the myocardium is to be performed based on a time at which the CT value of the TDC of the right ventricular indicates a peak. More specifically, the determination function 14b determines that the process of correcting the TDC of the myocardium is to be performed when a time at which the CT value of the TDC of the right ventricular indicates a peak and a time at which the CT value of the TDC of the myocardium indicates a maximum value fall within a predetermined time range. In other words, the determination function 14b determines that the process of correcting the TDC of the myocardium is to be performed when the TDC of the myocardium has a local peak at the same timing as the TDC of the right ventricular or when the TDC of the myocardium has a local peak at around a peak of the TDC of the right ventricular.

Alternatively, for example, the determination function 14b may determine that the process of correcting the TDC of the myocardium is to be performed when the CT value of the TDC of the myocardium indicates a maximum value between the time at which the CT value of the TDC of the right ventricular indicates a peak and the time at which the CT value of the TDC of the supply site that supplies blood to the myocardium indicates a peak.

If it is determined that the correction process on the TDC of the myocardium is to be performed (Yes at Step S4), the determination function 14b proceeds to Step S5. In contrast, if it is not determined that the correction process on the TDC of the myocardium is to be performed (No at Step S4), the determination function 14b proceeds to Step S6. Step S5 and Step S6 are steps corresponding to the correction function 14c. At these steps, the processing circuitry 14 calls a predetermined program corresponding to the correction function 14c from the memory 13 and executes the program, so that the correction function 14c is implemented.

At step S5, the correction function 14c performs the correction process on the TDC of the myocardium. In other words, if the determination function 14b determines that the process of correcting the TDC of the myocardium is to be performed, tine correction function 14c corrects the TDC of the myocardium. Here, the correction function 14c corrects the TDC of the myocardium based on the TDC of the right ventricular. For example, the correction function 14c corrects the TDC of the myocardium based on the time at which the CT value of the TDC of the right ventricular indicates a peak.

Figure 6:
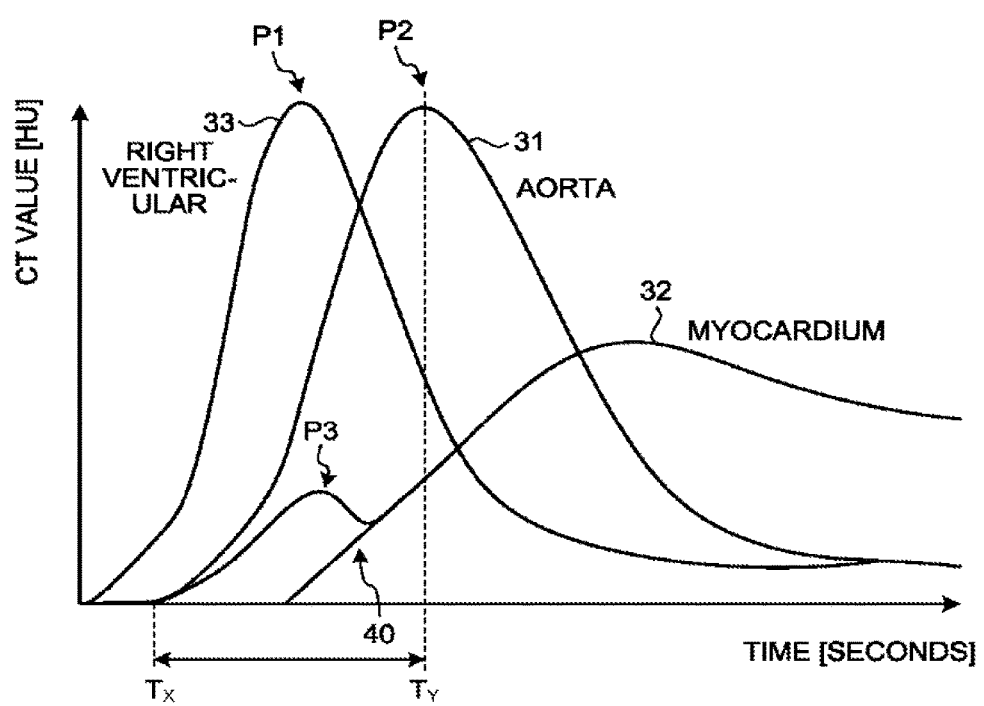
FIG. 6 is a diagram for explaining the first embodiment.

FIG. 6 is a diagram for explaining the first embodiment. The vertical axis in FIG. 6 represents a CT value (HU), and the horizontal axis in FIG. 6 represents a time (seconds). In FIG. 6, the TDC 31 of the aorta, the TDC 32 of the myocardium, and the TDC 33 of the right ventricular are illustrated. Here, a peak of the TDC 33 of the right ventricular is denoted by P1, and a peak of the TDC 31 of the aorta is denoted by P2. In the example illustrated in FIG. 6, the TDC 32 of the myocardium has a local peak (P3) at substantially the same timing as the peak (P1) of the TDC 33 of the right ventricular. In the example illustrated in FIG. 6, the correction function 14c corrects, by linear interpolation, the TDC 32 of the myocardium in a predetermined period corresponding to a period including the time indicating the peak (P1) of the TDC 33 of the right ventricular. For example, the correction function 14c sets a period from $T_x$ to $T_y$ illustrated in FIG. 6 as a period including the time of the peak (P1) of the TDC 33 of the right ventricular. The time $T_y$ is, for example, a time at which the TDC 31 of the aorta reaches the peak (P2). The time $T_x$ is, for example, a time at which the TDC 31 of the aorta starts to rise. The time $T_x$ may be, for example, a time at which the TDC 32 of the myocardium starts to rise. Further, the time $T_x$ may be, for example, a time at which the TDC 33 of the right ventricular has the maximum slope, or may be a time at around the time at which the TDC 33 of the right ventricular has the maximum slope.

The correction function 14c corrects the TDC 32 of the myocardium in the period from $T_x$ to $T_y$ by linear interpolation. In the example illustrated in FIG. 6, the correction function 14c obtains a TDC 40 of the myocardium by performing linear interpolation on the local peak (P3) that has occurred around the peak (P1) of the TDC 33 of the right ventricular.

Figure 7:
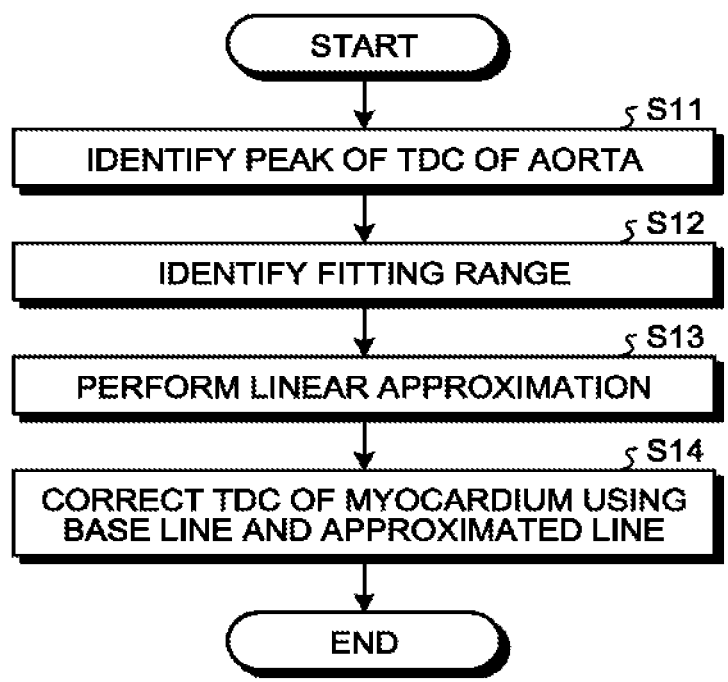
FIG. 7 is a flowchart illustrating a procedure in a process of correcting a TDC of a myocardium performed by a correction function according to the first embodiment.
Figure 8:
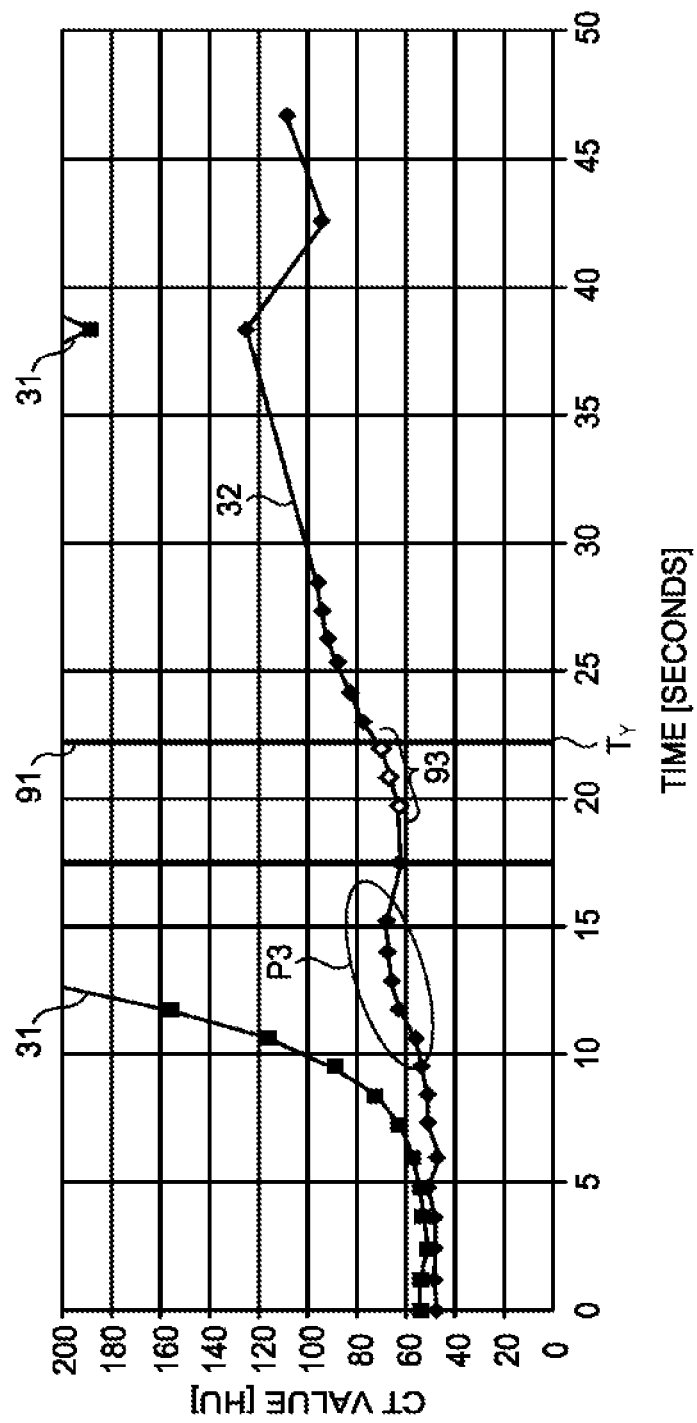
FIG. 8 is a diagram for explaining the first embodiment.
Figure 9:
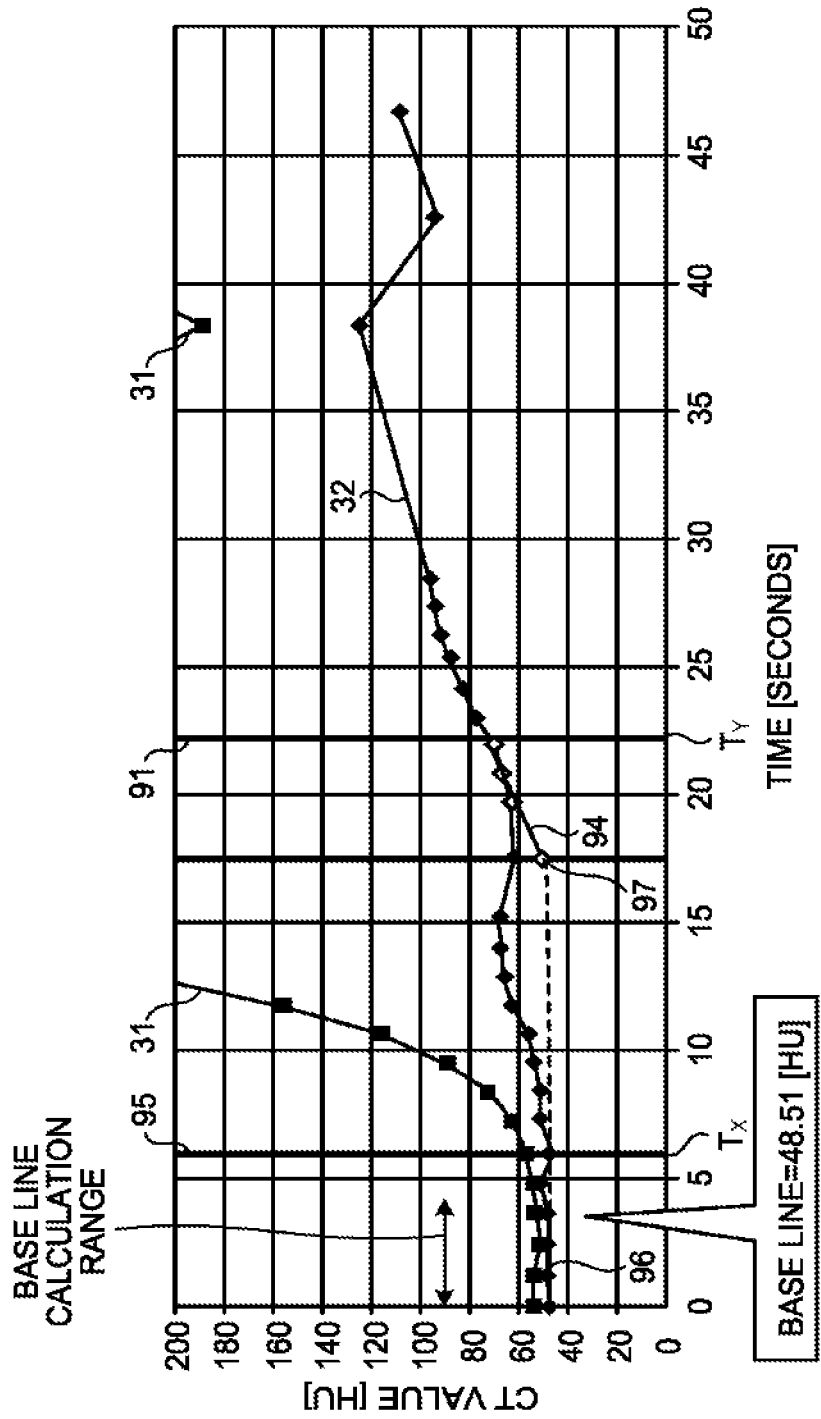
FIG. 9 is a diagram for explaining the first embodiment.

The correction process on the TDC of the myocardium performed by the correction function 14c will be described in detail below with reference to FIG. 7 to FIG. 9. FIG. 7 is a flowchart illustrating a procedure in the correction process on the TDC of the myocardium performed by the correction function 14c according to the first embodiment. FIG. 8 and FIG. 9 are diagrams for explaining the first embodiment. The flowchart illustrated in FIG. 7 corresponds to the process at Step S5 illustrated in FIG. 4. FIG. 8 and FIG. 9 illustrate parts of the TDC 31 of the aorta and the TDC 32 of the myocardium. The vertical axes in FIG. 8 and FIG. 9 represent CT values (HU), and the horizontal axes in FIG. 8 and FIG. 9 represent times (seconds).

As illustrated in FIG. 7, at Step S11, the correction function 14c identifies a peak of the TDC 31 of the aorta. More specifically, in the example illustrated in FIG. 8, the correction function 14c identifies a time $T_y$ at which the TDC 31 of the aorta reaches a peak. In FIG. 8, the time $T_y$ at which the TDC 31 of the aorta reaches the peak is indicated by a bold line 91. In FIG. 8, a local peak of the TDC 32 of the myocardium is denoted by P3.

At Step S12, the correction function 14c identifies a fitting range. Step S12 is a process of identifying data for approximating a line for linear interpolation. The time $T_y$ at which the TDC 31 of the aorta reaches the peak corresponds to the time at which the TDC 32 of the myocardium has the maximum slope. Further, a temporal change in the CT value at around the time at which the TDC 32 of the myocardium has the maximum slope is important in the myocardial perfusion. Therefore, the correction function 14c identifies data for approximating a line by using a temporal change in the CT value at around the time at which the TDC 32 of the myocardium has the maximum slope. For example, as illustrated in FIG. 8, the correction function 14c identifies, as a fitting range 93, sample points at times prior to the time $T_y$ by using the time $T_y$ of the peak of the TDC 31 of the aorta as a point of origin. FIG. 8 illustrates a case in which the correction function 14c identifies three points as the fitting range 93. The number of sample points to be identified as the fitting range by the correction function 14c is not limited to three as long as the sample points can approximate a line.

The description returns to FIG. 7. At Step S13, the correction function 14c performs linear approximation. For example, as illustrated in FIG. 9, the correction function 14c performs linear approximation using data of the three points that are identified as the fitting range 93 at Step S12. More specifically, the correction function 14c generates an approximated line 94 as illustrated in FIG. 9.

At Step S14, the correction function 14c corrects the TDC of the myocardium using a base line and the approximated line 94. For example, the correction function 14c first identifies the base line. Here, the base line indicates a CT value obtained when a contrast agent is not present, and is, for example, an average of CT values at a few points from the first point of the TDC 32 of the myocardium. As one example, as illustrated in FIG. 9, the correction function 14c calculates an average of CT values from the first to the fourth points of the TDC 32 of the myocardium and identifies a base line 96. FIG. 9 illustrates a case in which a CT value of the base line is 48.51 (HU). The correction function 14c may obtain, as the base line, an average of CT values of the TDC 32 of the myocardium from the first point to a point at the time $T_x$ at which the TDC 31 of the aorta starts to rise. In FIG. 9, the time $T_x$ at which the TDC 31 of the aorta starts to rise is indicated by a bold line 95.

The correction function 14c obtains an intersection 97 of an extended line of the base line 96 and an extended line of the approximated line 94. The correction function 14c corrects the TDC 32 of the myocardium such that the base line 96 and the intersection 97 are connected and the intersection 97 and the approximated line 94 are connected. In this manner, the correction function 14c corrects, by linear interpolation, the TDC 32 of the myocardium in a predetermined period (the period from $T_x$ to $T_y$ in FIG. 9) based on the time at which the CT value of the TDC of the supply site indicates a peak. After completion of Step S14, the correction function 14c proceeds to Step S6 in FIG. 4.

Figure 10:
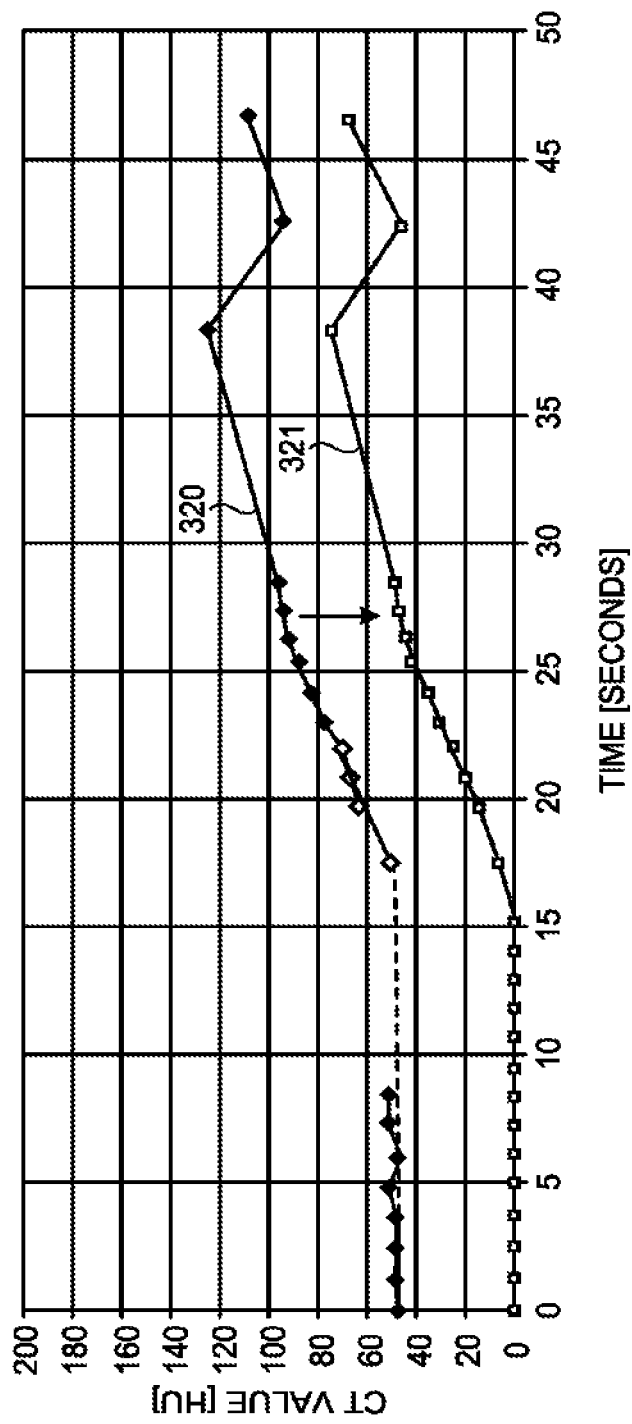
FIG. 10 is a diagram for explaining the first embodiment.

The description returns to FIG. 4. At Step S6, the correction function 14c corrects each of the TDCs using the base line. FIG. 10 is a diagram for explaining the first embodiment. In FIG. 10, only the TDC of the myocardium is illustrated for convenience of explanation.

The CT values of the TDCs illustrated in FIG. 8 and FIG. 9 include a CT value of a blood component that is colored due to the influence of the contrast agent and a CT value derived from a tissue that is independent of the influence of the contrast agent. In contrast, when the myocardial blood flow rate is calculated, the CT value derived from a tissue is eliminated and the CT value of the blood component is used. Therefore, the correction function 14c calculates, by use of the base line, the CT value of the blood component that is colored due to the influence of the contrast agent. In other words, the correction function 14c corrects, by the base line, each of the TDCs used for calculation of the myocardial blood flow rate.

More specifically, as illustrated in FIG. 10, the correction function 14c subtracts the base line from a TDC 320 of the myocardium that is obtained through the correction process at Step S5, and obtains a TDC 321 of the myocardium for which the base line is corrected. The correction function 14c corrects the TDC of the aorta using the base line in the same manner.

Step S7 is a step corresponding to the calculation function 14d. At this step, the processing circuitry 14 calls a predetermined program corresponding to the calculation function 14d from the memory 13 and executes the program, so that the calculation function 14d is implemented. At Step S7, the calculation function 14d calculates the myocardial blood flow rate. For example, the calculation function 14d calculates the myocardial blood flow rate by solving a transfer function using, as input, the TDC of the aorta that has been corrected by use of the base line at Step S6 and using, as output, the TDC of the myocardium that has been corrected by use of the base line at Step S6.

If it is determined that the correction process is to be performed at Step S4, the calculation function 14d calculates the myocardial blood flow rate by solving a transfer function using, as output, the TDC of the myocardium that has been corrected by use of the base line at Step S6 after the correction process at Step S5. After completion of Step S7, the processing circuitry 14 ends the process.

As described above, in the first embodiment, if the TDC of the myocardium is influenced by the artifact from the right ventricular, the medical image processing apparatus 10 generates a TDC of the myocardium for which the artifact from the right ventricular is corrected. For example, the medical image processing apparatus 10 corrects, by linear interpolation, the TDC of the myocardium in a predetermined period corresponding to a period including a time of the peak of the TDC of the right ventricular. Then, the medical image processing apparatus 10 calculates a myocardial blood flow rate using the TDC of the myocardium for which the artifact from the right ventricular is corrected. Consequently, according to the medical image processing apparatus 10 of the first embodiment, even when the TDC of the myocardium is influenced by the artifact from the right ventricular, it is possible to accurately calculate the myocardial blood flow rate.

Modification of First Embodiment

In the first embodiment described above, a case has been described in which, as the process at Step S5 in FIG. 4, the correction function 14c corrects, by linear interpolation, the TDC of the myocardium in a predetermined period corresponding to a period including the time of the peak of the TDC of the right ventricular; however, possible embodiments are not limited to this example. For example, if there is an influence of the TDC of the right ventricular as an artifact, the TDC of the right ventricular is added to the TDC of the myocardium at a predetermined ratio. In view of this, the correction function 14c according to a modification of the first embodiment may correct the TDC of the myocardium by eliminating the TDC of the right ventricular that has an influence as the artifact. In the following, as the modification of the first embodiment, a case will be described in which, as the process at Step S5 illustrated in FIG. 4, the correction function 14c performs a scaling process on the TDC of the right ventricular in a certain period including the time of the peak, and thereafter performs a process of subtracting a TDC obtained through the scaling process from the TDC of the myocardium to thereby correct the TDC of the myocardium.

Figure 11:
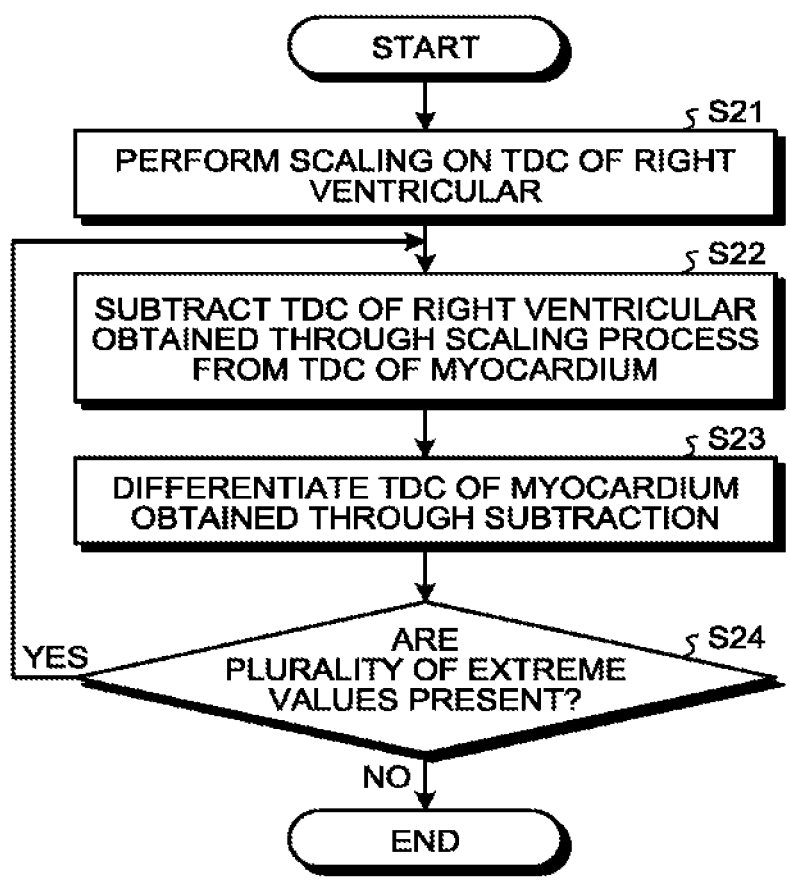
FIG. 11 is a flowchart illustrating a procedure in a process of correcting a TDC of a myocardium performed by a correction function according to a modification of the first embodiment.
Figure 12:
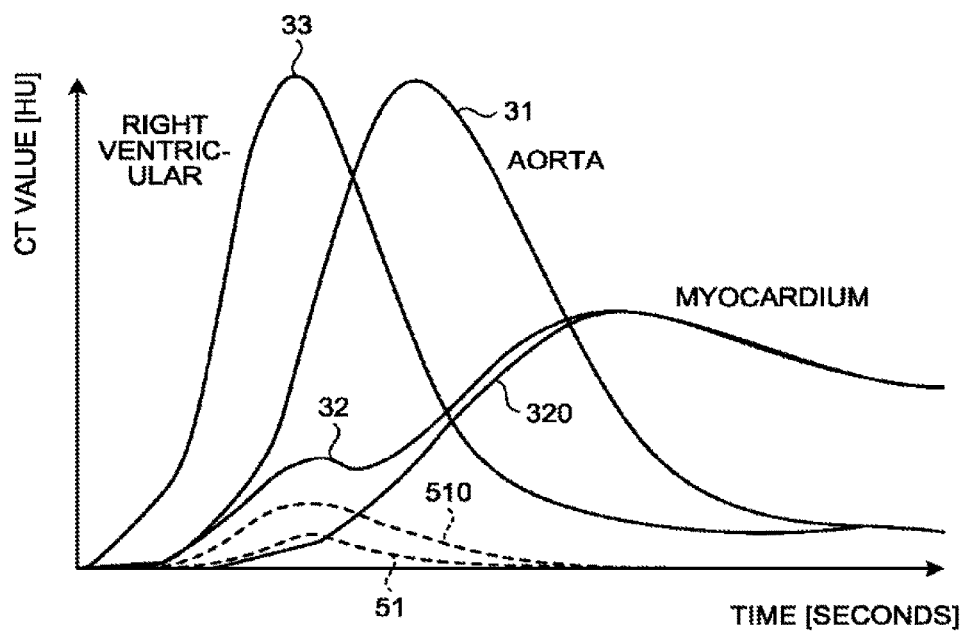
FIG. 12 is a diagram for explaining the modification of the first embodiment.

FIG. 11 is a flowchart illustrating a procedure in a process of correcting the TDC of the myocardium by the correction function 14c according to the modification of the first embodiment. FIG. 12 is a diagram for explaining the modification of the first embodiment. The flowchart illustrated in FIG. 11 corresponds to the process at Step S5 illustrated in FIG. 4. The vertical axis in FIG. 12 represents a CT value (HU), and the horizontal axis in FIG. 12 represents a time (seconds). In FIG. 12, the TDC 31 of the aorta, the TDC 32 of the myocardium obtained before correction, and the TDC 33 of the right ventricular are illustrated. In FIG. 12, the TDC 320 of the myocardium corrected by the scaling process is also illustrated.

As illustrated in FIG. 11, at Step S21, the correction function 14c performs scaling on the TDC of the right ventricular. Here, the correction function 14c performs scaling on the TDC of the right ventricular using a coefficient set in advance. For example, as illustrated in FIG. 12, the correction function 14c performs a scaling process on the TDC 33 of the right ventricular in a certain period including a time of the peak, and obtains a TDC 51 after the scaling process.

At Step S22, the correction function 14c subtracts the TDC of the right ventricular subjected to the scaling from the TDC of the myocardium. For example, the correction function 14c performs a process of subtracting the TDC 51 obtained through the scaling process as illustrated in FIG. 12 from the TDC 32 of the myocardium obtained before the correction. Subsequently, at Step S23, the correction function 14c differentiates the TDC of the myocardium obtained through the subtraction. At Step S24, the correction function 14c determines whether a plurality of extreme values is present.

If it is determined that a plurality of extreme values are present (Yes at Step S24), the correction function 14c proceeds to Step S22, and repeats the processes from Step S22 to Step S24 until it is not determined that a plurality of extreme values are present. In other words, the correction function 14c performs a scaling process such that a single extreme value is obtained when the TDC of the myocardium obtained through multiple times of the subtraction process is differentiated.

In contrast, if it is not determined that a plurality of extreme values are present (No at Step S24), the correction function 14c ends the process. For example, it is assumed that the correction function 14c performs, a total of n times, a process of subtracting the TDC 51 obtained through the scaling process from the TDC 32 of the myocardium obtained before the correction, and obtains a state in which a plurality of extreme values are not present. In this case, assuming that a TDC 510 illustrated in FIG. 12 is obtained by multiplying the TDC 51 obtained through the scaling process by n, the correction function 14c subtracts the TDC 510 from the TDC 320 of the myocardium obtained before the correction, and obtains the TDC 320 of the myocardium corrected through the scaling process. In this manner, the correction function 14c corrects the TDC of the myocardium by subtracting the TDC obtained through the scaling process from the TDC of the myocardium.

As described above, in the modification of the first embodiment, when the TDC of the myocardium is influenced by the artifact from the right ventricular, the medical image processing apparatus 10 generates the TDC of the myocardium for which the artifact from the right ventricular is corrected. For example, the medical image processing apparatus 10 performs a scaling process on the TDC of the right ventricular in a certain period including the time of the peak, and subtracts the TDC obtained through the scaling process from the TDC of the myocardium to thereby correct the TDC of the myocardium. Then, the medical image processing apparatus 10 calculates the myocardial blood flow rate using the TDC of the myocardium for which the artifact from the right ventricular is corrected. Therefore, according to the medical image processing apparatus 10 of the modification of the first embodiment, even when the TDC of the myocardium is influenced by the artifact from the right ventricular, it is possible to accurately calculate the myocardial blood flow rate.

In the examples illustrated in FIG. 11 and FIG. 12, a case has been described in which scaling is performed on the TDC of the right ventricular multiple times using a coefficient that is set in advance; however, possible embodiments are not limited to this example. For example, the correction function 14c may set a coefficient for the scaling using the least squares method. In other words, the correction function 14c performs a scaling process such that a single extreme value is obtained when the TDC of the myocardium obtained through the subtraction process is differentiated.

Other Embodiments

Possible embodiments are not limited to the embodiments described above.

In the embodiments described above, a case has been described in which the medical image processing apparatus 10 generates TDCs; however, possible embodiments are not limited to this example. For example, the X-ray CT apparatus 2 may generate TDCs. In this case, the X-ray CT apparatus 2 receives setting of ROIs in X-ray CT images, and generates TDCs indicating temporal changes in CT values in the set ROIs. The medical image processing apparatus 10 acquires the TDCs generated by the X-ray CT apparatus 2, and corrects the TDC of the myocardium based on the TDC of the right ventricular.

Further, in the embodiments described above, a case has been described in which the medical image processing apparatus 10 performs a process of correcting the TDC of the myocardium; however, possible embodiments are not limited to this example. For example, the X-ray CT apparatus 2 may perform the process of correcting the TDC of the myocardium.

Furthermore, in the embodiments described above, a case has been described in which a TDC is adopted as the change information indicating a temporal change in a CT value; however, possible embodiments are not limited to this example. For example, an expression form of the change information indicating a temporal change in the CT value can be arbitrarily changed as long as a time and the CT value are associated in the information.

In the embodiments described above, a case has been described in which the aorta is adopted as the supply site that supplies blood to the myocardium; however, possible embodiments are not limited to this example. For example, the supply site may be the left ventricular or the coronary artery.

The word "processor" used in the above description means, for example, a central processing unit (CPU), a graphics processing unit (GPU), or a circuit, such as an application specific integrated circuit (ASIC) and a programmable logic device (for example, a simple programmable logic device (SPLD), a complex programmable logic device (CPLD), and a field programmable gate array (FPGA)). The processor reads and executes programs stored in a memory to implement functions. The programs may be directly embedded in the circuit of the processor, instead of storing the programs in the memory. In this case, the processor reads and executes the programs embedded in the circuit to implement the functions. Each of the processors in the embodiment does not necessarily have to be configured as a single circuit. Alternatively, a plurality of independent circuits may be combined into a single processor that implements corresponding functions. Further, a plurality of components illustrated in FIG. 1 may be integrated into a single processor that implements corresponding functions.

The components of the apparatuses illustrated in the drawings of the embodiment described above are merely conceptual, and need not be physically configured in the manner illustrated in the drawings. In other words, specific forms of distribution and integration of the apparatuses are not limited to those illustrated in the drawings, and all or part of the apparatuses may be functionally or physically distributed or integrated in arbitrary units depending on various loads or use conditions. Further, for each processing function performed by each apparatus, all or any part of the processing function may be implemented by a CPU and a program analyzed and executed by the CPU or may be implemented as hardware by wired logic.

Further, the control method explained in the embodiment described above may be implemented by causing a computer, such as a personal computer or a workstation, to execute a control program prepared in advance. The control program may be distributed via a network, such as the Internet. The control program may be stored in a computer-readable recording medium, such as a hard disk, a flexible disk (FD), a compact disc read only memory (CD-ROM), a magneto-optical disk (MO), or a digital versatile disk (DVD), and may be executed by the computer by being read from the recording medium.

According to at least one of the embodiments described above, it is possible to accurately calculate a myocardial blood flow rate.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
processing circuitry configured to
acquire pieces of change information indicating temporal changes in computed tomography (CT) values of a myocardium and a right ventricular of a subject based on a plurality of chronologically consecutive images that are generated by an X-ray CT apparatus by scanning the subject to which a contrast agent is administered; and
correct the piece of change information on the myocardium based on the piece of change information on the right ventricular.

2. The image processing apparatus according to claim 1, wherein the processing circuitry is configured to correct the piece of change information on the myocardium based on a time at which the CT value of the piece of change information on the right ventricular indicates a peak.

3. The image processing apparatus according to claim 2, wherein the processing circuitry is configured to correct, by linear interpolation, the piece of change information on the myocardium in a predetermined period including the time indicating the peak of the piece of change information on the right ventricular.

4. The image processing apparatus according to claim 3, wherein
the processing circuitry is configured to
acquire a piece of change information on a blood vessel that supplies blood to the myocardium, and
correct, by linear interpolation, the piece of change information on the myocardium in the predetermined period based on a time at which a CT value of the piece of change information on the blood vessel indicates a peak.

5. The image processing apparatus according to claim 2, wherein the processing circuitry is configured to perform a scaling process on the piece of change information on the right ventricular in a certain period including the time indicating the peak, and perform a subtraction process of subtracting the piece of change information obtained through the scaling process from the piece of change information on the myocardium to thereby correct the piece of change information on the myocardium.

6. The image processing apparatus according to claim 5, wherein the processing circuitry is configured to perform the scaling process such that a single extreme value is obtained when the piece of change information on the myocardium obtained through the subtraction process is differentiated.

7. The image processing apparatus according to claim 6, wherein the processing circuitry is configured to perform the scaling process such that a single extreme value is obtained when the piece of change information on the myocardium obtained through multiple times of the subtraction process is differentiated.

8. The image processing apparatus according to claim 1, wherein the processing circuitry is further configured to determine whether a correction process on the piece of change information on the myocardium is to be performed based on a time at which the CT value of the piece of change information on the right ventricular indicates a peak, the processing circuitry is configured to correct, when the correction process on the piece of change information on the myocardium is to be performed, the piece of change information on the myocardium.

9. The image processing apparatus according to claim 8, wherein when a time at which the CT value of the piece of change information on the right ventricular indicates a peak and a time at which the CT value of the piece of change information on the myocardium indicates a maximum value fall within a predetermined time range, the processing circuitry is configured to determine that the correction process on the piece of change information on the myocardium is to be performed.

10. The image processing apparatus according to claim 8, wherein when the CT value of the piece of change information on the myocardium indicates a maximum value between the time at which the CT value of the piece of change information on the right ventricular indicates a peak and the time at which the CT value of the piece of change information on the blood vessel that supplies blood to the myocardium indicates a peak, the processing circuitry is configured to determine that the correction process on the change information on the myocardium is to be performed.

* * * * *